(12) United States Patent
Tang et al.

(10) Patent No.: US 9,051,598 B2
(45) Date of Patent: Jun. 9, 2015

(54) SPECIFIC DETECTION OF D-GLUCOSE BY A TETRAPHENYLETHENE-BASE FLUORESCENT SENSOR

(75) Inventors: Benzhong Tang, Kowloon (HK); Yi Liu, Hangzhou (CN); Jingzhi Sun, Hangzbu (CN); Anjun Qin, Hangzhou (CN); Rongrong Hu, Kowloon (HK)

(73) Assignee: THE HONG KONG UNIVERSITY OF SCIENCE AND TECHNOLOGY, Hong Kong (CN)

( * ) Notice: Subject to any disclaimer, the term of this patent is extended or adjusted under 35 U.S.C. 154(b) by 316 days.

(21) Appl. No.: 13/462,183

(22) Filed: May 2, 2012

(65) Prior Publication Data

US 2012/0282703 A1    Nov. 8, 2012

Related U.S. Application Data (60) Provisional application No. 61/457,610, filed on May 2, 2011.

(51) Int. Cl.
| | |
|---|---|
| *G01N 21/64* | (2006.01) |
| *G01N 33/52* | (2006.01) |
| *C12Q 1/54* | (2006.01) |
| *G01N 33/66* | (2006.01) |
| *G01N 33/58* | (2006.01) |

(52) U.S. Cl.
CPC .......... *C12Q 1/54* (2013.01); *Y10T 436/144444* (2015.01); *G01N 21/64* (2013.01); *G01N 33/52* (2013.01); *G01N 21/6428* (2013.01); *G01N 33/66* (2013.01); *G01N 33/582* (2013.01); *G01N 21/6486* (2013.01); *G01N 2021/6439* (2013.01)

(58) Field of Classification Search
CPC .............. G01N 21/64; G01N 21/6428; G01N 21/6486; G01N 33/52; G01N 33/582; G01N 33/66; G01N 2021/64; G01N 2021/6428; G01N 2021/6439
USPC ...................................... 436/93–95, 166, 172
See application file for complete search history.

(56) References Cited

U.S. PATENT DOCUMENTS

| | | | |
|---|---|---|---|
| 5,503,770 A | 4/1996 | James et al. | |
| 5,763,238 A * | 6/1998 | James et al. | 436/172 |
| 6,344,360 B1 * | 2/2002 | Colvin et al. | 436/94 |
| 6,713,566 B1 * | 3/2004 | Marcuccio et al. | 525/337 |
| 7,751,863 B2 * | 7/2010 | Markle et al. | 600/317 |

(Continued)

OTHER PUBLICATIONS

Yoon, J. et al, Journal of the American Chemical Society 1992, 114, 5874-5875.*

(Continued)

*Primary Examiner* — Arlen Soderquist
(74) *Attorney, Agent, or Firm* — Nath, Goldberg & Meyer; Joshua B. Goldberg (57) ABSTRACT

A method of detecting the presence or absence of saccharide or saccharide level in a biological or artificial sample comprising contacting the sample with a water-soluble tetraphenylethene-cored probe having multiple functionalities of boronic acid and aggregation induced emission (AIE) characteristics, and detecting fluorescence. A method for detecting pH in a sample solution with a certain pH value comprising contacting the sample solution with a water-soluble tetraphenylethene-cored probe having multiple functionalities of boronic acid and aggregation induced emission (AIE) characteristics, and detecting fluorescence.

21 Claims, 9 Drawing Sheets

(56) References Cited

U.S. PATENT DOCUMENTS

| | | | |
|---|---|---|---|
| 8,498,682 B2* | 7/2013 | Markle et al. | 600/317 |
| 2004/0048390 A1 | 3/2004 | Wang et al. | |
| 2006/0240565 A1* | 10/2006 | Tang et al. | 436/164 |
| 2007/0030443 A1* | 2/2007 | Chapoy et al. | 351/160 R |
| 2008/0145944 A1* | 6/2008 | Colvin et al. | 436/95 |
| 2008/0188722 A1* | 8/2008 | Markle et al. | 600/316 |
| 2008/0188725 A1* | 8/2008 | Markle et al. | 600/316 |
| 2009/0155183 A1 | 6/2009 | Clark | |
| 2010/0009362 A1* | 1/2010 | Tang et al. | 435/6 |
| 2010/0274110 A1 | 10/2010 | Markle et al. | |
| 2010/0297016 A1* | 11/2010 | Geddes et al. | 424/9.1 |
| 2011/0224516 A1* | 9/2011 | Romey et al. | 600/317 |

OTHER PUBLICATIONS

Shiomi, Y. et al, Journal of the Chemical Society Perkin Transactions I 1993, 2111-2117.*
Samankumara, K. R. A. et al, Journal of the Chemical Society Chemical Communications 1994, 1621-1692.*
Suenaga, H. et al, Tetrahedron Letters 1995, 36, 4825-4828.*
Takeuchi, M. et al, Tetrahedron 1997, 53, 8335-8348.*
Eggert, H. et al, Journal of Organic Chemistry 1999, 64, 3846-3852.*
Yuan, W. Z. et al, Advanced Materials 2010, 22, 2159-2163.*
Liu, Y. et al, Journal of the American Chemical Society 2011, 133, 660-663.*
Shimpuku, et al., "Selective glucose recognition by boronic acid azoprobe/γ-cyclodextrin complexes in water," Chem. Commun., (2009), pp. 1709-1711.
James, et al., "Novel Saccharide-Photoinduced Electron Transfer Sensors Based on the Interaction of Boronic Acid and Amine," J. Am. Chem. Soc., (1995), vol. 117, pp. 8982-8987.
James, "Saccharide-Selective Boronic Acid Based Photoinduced Electron Transfer (PET) Fluorescent Sensors," Top Curr Chem, (2007), vol. 277, pp. 107-152.
Karnati, et al., "A Glucose-Selective Fluorescence Sensor Based on Boronic Acid-Diol Recognition," Bioorganic & Medicinal Chemistry Letters, (2002), vol. 12, pp. 3373-3377.
Hargrove et al., Boronic Acid Porphyrin Receptor for Ginsenoside Sensing, Organic Letters, 2010, vol. 12, No. 21, pp. 4804-4807.
Huang et al., Glucose Sensing via Aggregation and the Use of "Knock-Out" Binding to Improve Selectivity, J. Am. Chem. Soc., 2013, 135, 1700-1703.

* cited by examiner

SPECIFIC DETECTION OF D-GLUCOSE BY A TETRAPHENYLETHENE-BASE FLUORESCENT SENSOR

CROSS REFERENCE TO RELATED APPLICATION

Pursuant to 35 U.S.C. §119(e), this application claims the benefit of Provisional Application No. 61/457,610 filed on May 2, 2011, which application is hereby incorporated by reference in its entirety.

FIELD OF THE PRESENT SUBJECT MATTER

The present subject matter relates to a detection of saccharide in a sample using a tetraphenylethene (TPE)-based fluorescent sensor. In particular, the present subject matter relates to a detection of the presence or absence of glucose or the glucose level in a sample using a TPE-based fluorescent sensor. In addition, the present subject matter relates to a detection method of a pH in a sample solution.

BACKGROUND OF THE PRESENT SUBJECT MATTER

Fluorescent (FL) technique has emerged as a mainstream research and development area in science and engineering, particularly in the field of analytic chemistry and biological science, thanks to its high sensitivity, low-background noise and broad dynamic range, etc. A great number of fluorescent probes have been investigated and widely used in biotechnology.

Since the chemistry of saccharide and related molecular species plays a significant role in the metabolic pathway of living organisms, determining the presence and concentration of biologically important sugars in aqueous media solution, particularly D-glucose (Glu) which is a ubiquitous fuel for biological processes, is necessary in various medicinal and industrial contexts, such as diabetic monitoring. However, distinguishing D-Glu from other structurally similar monosaccharides, such as D-galactose (Gal), D-fructose (Fru) and D-mannose (Man) remains a daunting challenge, although the pioneering works have been done by Shinkai and coworkers (T. D. James, et al. Nature, 1995, 374, 345).

Through elaborate molecular structural designs, FL sensors with preferential binding to Glu have been developed in the past decade (T. D. James, et al. J. Am. Chem. Soc. 1995, 117, 8982; V. V. Karnati, et al. Bioorg. Med. Chem. Lett. 2002, 12, 3373; H. Eggert, et al. J. Org. Chem. 1999, 64, 3846; U.S. Pat. No. 5,503,770; U.S. Pat. No. 5,763,238). In a typical example, two phenylboronic acid (PBA) units were attached to a fluorophoric molecule at the "correct" positions to ensure the formation of 1:1 complex between the PBA probe and Glu analyte. A photoinduced electron transfer process was utilized to incite an FL turn-on response to the Glu binding. The Glu selectivity of such an affinity-dependent FL sensor, however, is rather limited because the PBA unit has a stronger affinity to other saccharides (e.g., Fru, Gal, and Man) than to Glu.

Accordingly, there has been a need in the art to develop new FL sensors with improved Glu selectivity. For this, new approaches based on new concepts need to be devised to exclude these non-Glu saccharides from participating in the FL turn-on processes.

In the mean time, it has been recently discovered that a group of nonemissive fluorogenic molecules, such as TPE, are induced to fluoresce efficiently by aggregate formation, so called an "abnormal" phenomenon of aggregation-induced emission (AIE). Both experimental data and theoretic calculations support the rationale that the unusual AIE effect is caused by the restriction of the intramolecular rotation (RIR) process of the phenyl rotors in the aggregate state. See U.S. Patent Application Publication Nos. 2008/0220407; 2008/0009362; 2010/0009362. See also W. Z. Yuan, Adv. Mater. 2010, 22, 2159.

SUMMARY OF THE PRESENT SUBJECT MATTER

To develop Glu-specific biosensors operating in conceptually new mechanisms, it has been envisioned by the present inventors that the RIR mechanism may be utilized to generate new FL biosensors for specific Glu detection. Two boronic acid-functionalized TPE derivatives were adopted: one is a bis(boronic acid)-functionalized TPE derivative, "1,2-diphenylethene-1,2-diyl)bis(1,4-phenylene)-1,1'-diboronic acid" (TPEDB, U.S. Patent Application Publication Nos. 2008/0220407; 2008/0009362) and the other was mono(boronic acid)-functionalized TPE derivative "4-(1,2,2-Triphenylvinyl)phenylboronic acid" (TPEMB, W. Z. Yuan, Adv. Mater. 2010, 22, 2159). TPEDB has been applied in the fields of DNA detection and protein quantitation, but never tried for detecting saccharide, particularly for selective detection of Glu.

As discussed herein, the emission of TPEDB can be boosted by the addition of Glu. More interestingly, it has been found that TPEDB is capable of distinguishing Glu from three other monosaccharides (Fru, Gal, and Man), which nearly had no effect on the emission of TPEDB. Further, it has been found that the boronic acid groups on TPEDB can react with diols on D-Glu to produce highly emissive oligomers. Other monosaccharides, such as Fru, Gal, and Man, however, could not oligomerize with TPEDB, thus no FL intensity increase happens. Accordingly, TPEDB can be a glucose-specific fluorescent sensor which can be used to detect the presence or absence of glucose or the glucose level in a sample, particularly in a biological sample taken from a host or one that is artificially prepared.

It has been also found that TPEDB luminogen is readily soluble in alkaline aqueous media containing small amount of DMSO (Dimethyl Sulfoxide). However, when below a pH of 9.0, TPEDB luminogen is highly emissive, suggesting that this probe can be utilized as a pH indicator that can be used as an environmental monitor.

In accordance, one aspect of the present subject matter relates to a method for detecting the presence or absence of glucose or the glucose level in a sample, comprising contacting the sample with a water-soluble tetraphenylethene (TPE)-cored probe having multiple functionalities of boronic acid and aggregation-induced emission (AIE) characteristics, and detecting fluorescence. In one embodiment, the TPE-cored probe is preferably TPEDB. In another embodiment, the emission of TPEDB can be boosted nearly 5.4 fold when the concentration of Glu reaches 5.0 mM. In still another embodiment, the sample can be a biological sample, such as urine, and the probe may selectively detect urine Glu. Thus, the water-soluble TPE-cored probe can be applied to monitor the urine Glu level of diabetics or potential diabetics.

Another aspect of the present subject matter relates to a method for detecting pH in a sample solution with a certain pH value, comprising contacting the sample solution with a water-soluble tetraphenylethene-cored probe having multiple functionalities of boronic acid and aggregation-induced emission (AIE) characteristics, and detecting fluorescence. In one embodiment, the water-soluble tetraphenylethene-cored probe can preferably be TPEDB. In another embodiment, the sample solution can be a sodium hydroxide solution. Since the probe has a great fluorescent response to pH, it can be used as an environmental monitor.

DETAILED DESCRIPTION OF THE PRESENT SUBJECT MATTER

The following definitions are provided for the purpose of understanding the present subject matter and for constructing the appended patent claims.

It is noted that, as used in this specification and the appended claims, the singular forms "a," "an" and "the" include plural references unless the context clearly dictates otherwise.

"Aggregation-induced emission" or AIE, as used herein refers to the fluorescence turned on upon aggregation formation. When molecularly dissolved, the material is nonemissive. However, when the intramolecular rotation is restricted the emission is turned on. In accordance, "aggregation-induced emission characteristics" as used herein refers to aggregation-induced emission activity. That is, when a compound has AIE characteristics the compound is AIE active, producing emission/fluorescence when it is aggregated.

"Emission intensity" as used herein refers to the magnitude of fluorescence normally obtained from a fluorescence spectrometer.

"Sample" as used herein refers to any sample which may contain a saccharide for which detection or an assay is desired. The sample may be a solution of D-glucose, D-galactose, D-mannose or D-fructose. The sample may be a biological sample, such as a biological fluid from a host or, may be artificially prepared, for example, urine, blood, plasma, serum, saliva, semen, stool, sputum, cerebral spinal fluid, tears, mucus, amniotic fluid or the like. The biological sample may also be a biological tissue that may exist in a solution. Biological tissue refers to an aggregate of cells, usually of a particular kind together with their intercellular substance that forms one of the structural materials of a human, animal, plant, bacterial, fungal or viral structure, including connective tissue, epithelium, muscle tissue, and nerve tissues. Non-limiting examples of biological tissues include organs, tumors, lymph nodes, arteries and individual cells.

Unless defined otherwise all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language; however, it will be understood by one of skill in the art, that in some specific instances, an embodiment can alternatively be described using the language "consisting essentially of" or "consisting of."

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In one aspect, the present subject matter relates to a method for detecting the presence or absence of glucose or the glucose level in a sample, comprising contacting the sample with a water-soluble tetraphenylethene-cored probe having multiple functionalities of boronic acid and aggregation-induced emission (AIE) characteristics, and detecting fluorescence. In an embodiment, the water-soluble TPE-cored prove is functionalized by diboronic acid, such as for example, TPE-diboronic acid (TPEDB).

TPEDB was synthesized by a two-step method as shown below. Because of self condensation of boronic acid with heating, no accurate elemental analysis data for TPEDB could be obtained. Its pinacol-protected derivative 3 was therefore prepared and characterized by elemental analysis. Satisfactory results were obtained.

3

For comparison, the analogue of mono(boronic acid) substituted TPE, named TPEMB was prepared via a three step reaction and its pinacol-protected derivative 7 was also prepared for elemental analysis.

To expand the types of TPE-cored boronic acid, TPEDPB was also prepared and characterized. Its synthetic routes were shown below.

Figure 1:
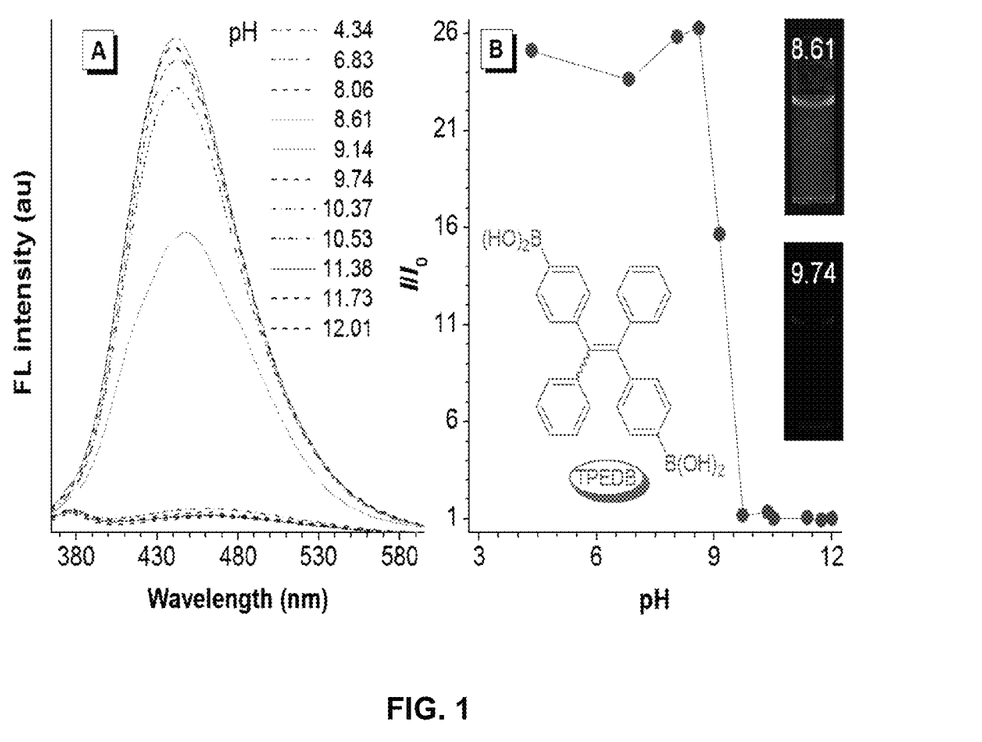
FIG. 1 illustrates (A) FL spectra of TPEDB (10 μM) in Britton-Robinson buffers containing 2 vol % DMSO at different pH values and (B) change in the FL intensity (I) of TPEDB at 440 nm with pH; $I_0$=intensity at pH 12.01. Inset: photographs of the mixtures of TPEDB in the aqueous buffers at pH 8.6 and 9.7 taken under illumination of a hand-held UV lamp ($\lambda_{ex}$=365 nm).

The obtained TPE-diboronic acid adduct TPEDB was immiscible with water, and when its aggregates were suspended in an acidic buffer (pH 4.34), they emitted a strong blue light. See FIG. 1. The light emission of TPEDB started to decrease in intensity when the pH of the buffer was raised to >8.61 and became very weak at pH≥9.74. Since the pKa of PBA is ca. 9, TPEDB was ionized by the alkaline medium and became soluble in the buffers with high pH. The solutions of TPEDB were virtually nonfluorescent, while its aggregates were highly emissive, proving that TPEDB, like its parent form TPE, is AIE-active.

Figure 2:
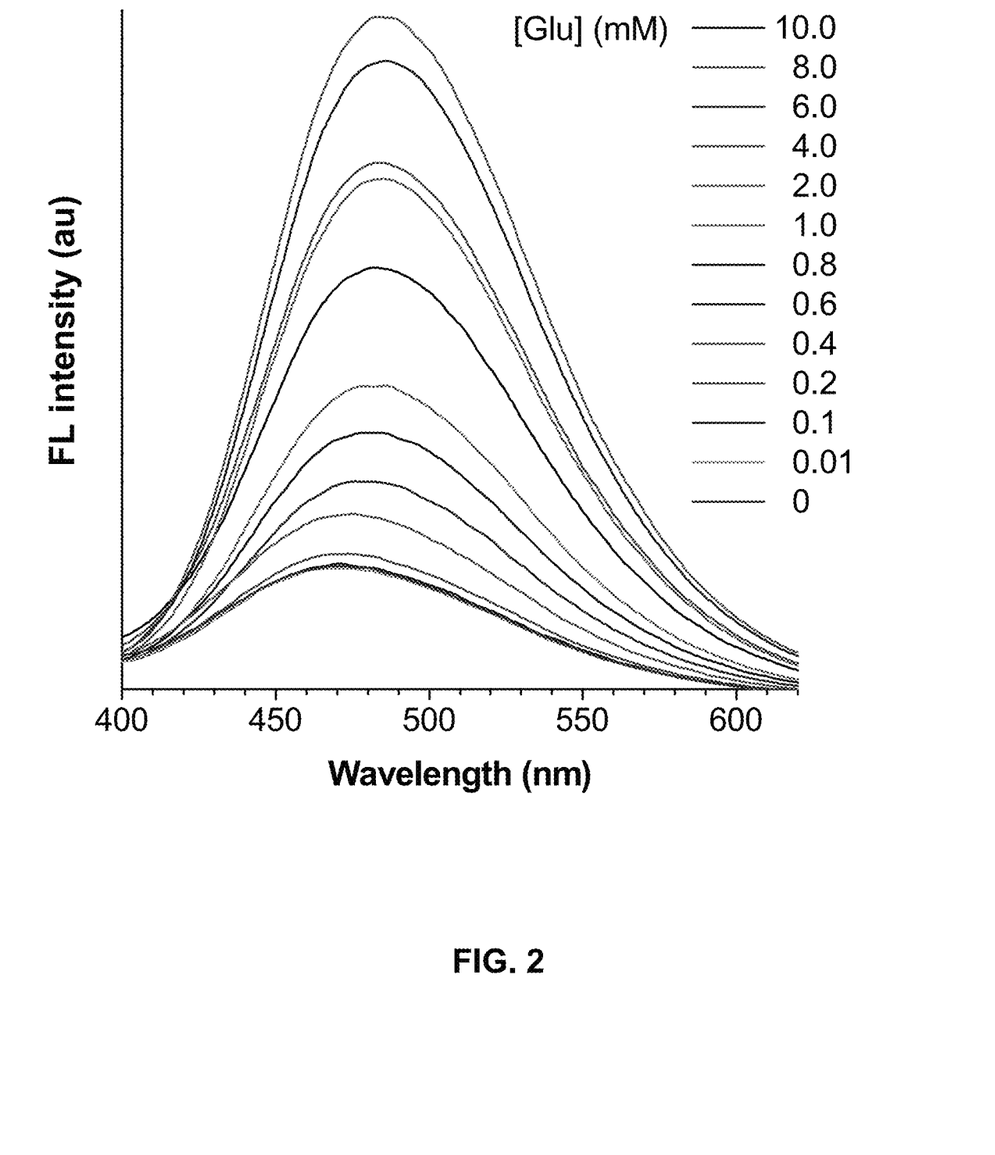
FIG. 2 illustrates FL spectra of TPEDB (50 μM) in the carbonate buffer containing 2 vol % DMSO (pH 10.5) in the presence of D-glucose.
Figure 3:
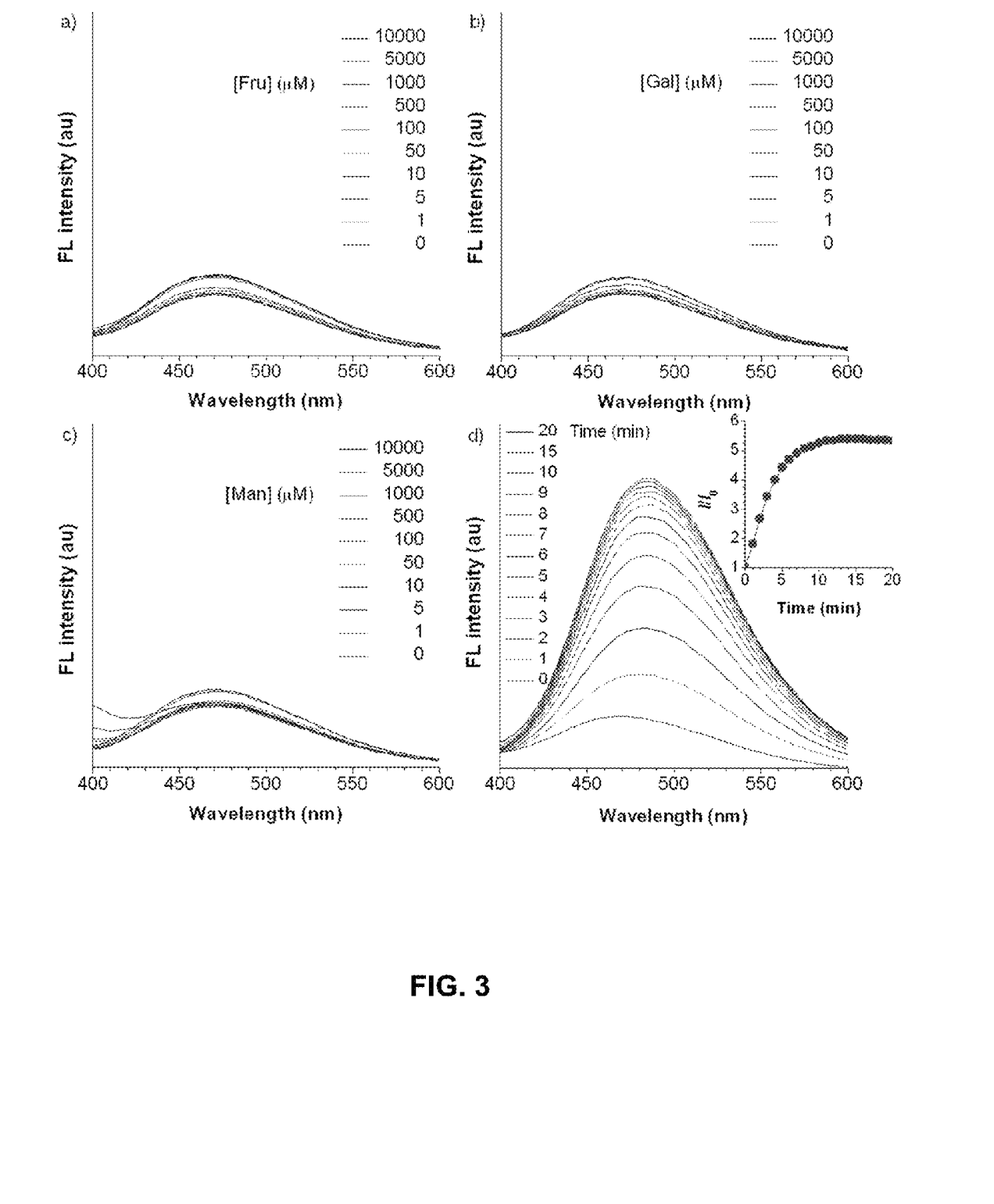
FIG. 3 illustrates FL spectra of mixtures of TPEDB (50 μM) in the carbonate buffer containing 2 vol % DMSO in the presence of different amounts of (a) D-fructose, (b) D-galactose, and (c) D-mannose. The figure (d) of FIG. 3 illustrates real-time monitoring of the reaction of D-glucose (5 mM) with TPEDB (50 μM) by the spectral change in the carbonate buffer. Inset: Variation in the FL intensity of the mixture of TPEDB (50 μM) and D-glucose (5 mM) with time in the carbonate buffer.
Figure 5:
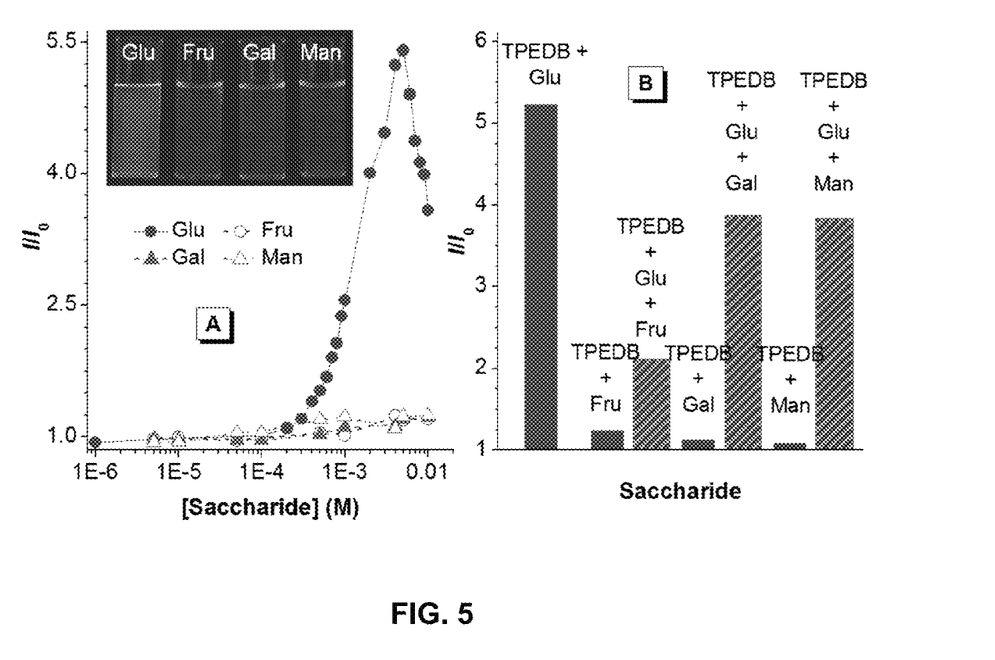
FIG. 5 illustrates (A) variation in the intensity (I) of TPEDB (50 μM) at 485 nm with a concentration of a saccharide in the carbonate buffer containing 2 vol % DMSO (pH=10.5) and (B) FL response of TPEDB (50 μM) to a saccharide (4 mM; red solid bar) other than Glu or to Glu in the presence of another saccharide interferent (0.1 mM; olive shaded bar). $I_0$=intensity in the absence of a saccharide. Inset: photographs of mixtures of TPEDB in the carbonate buffers containing 5 mM of a saccharide taken under UV illumination.
Figure 6:
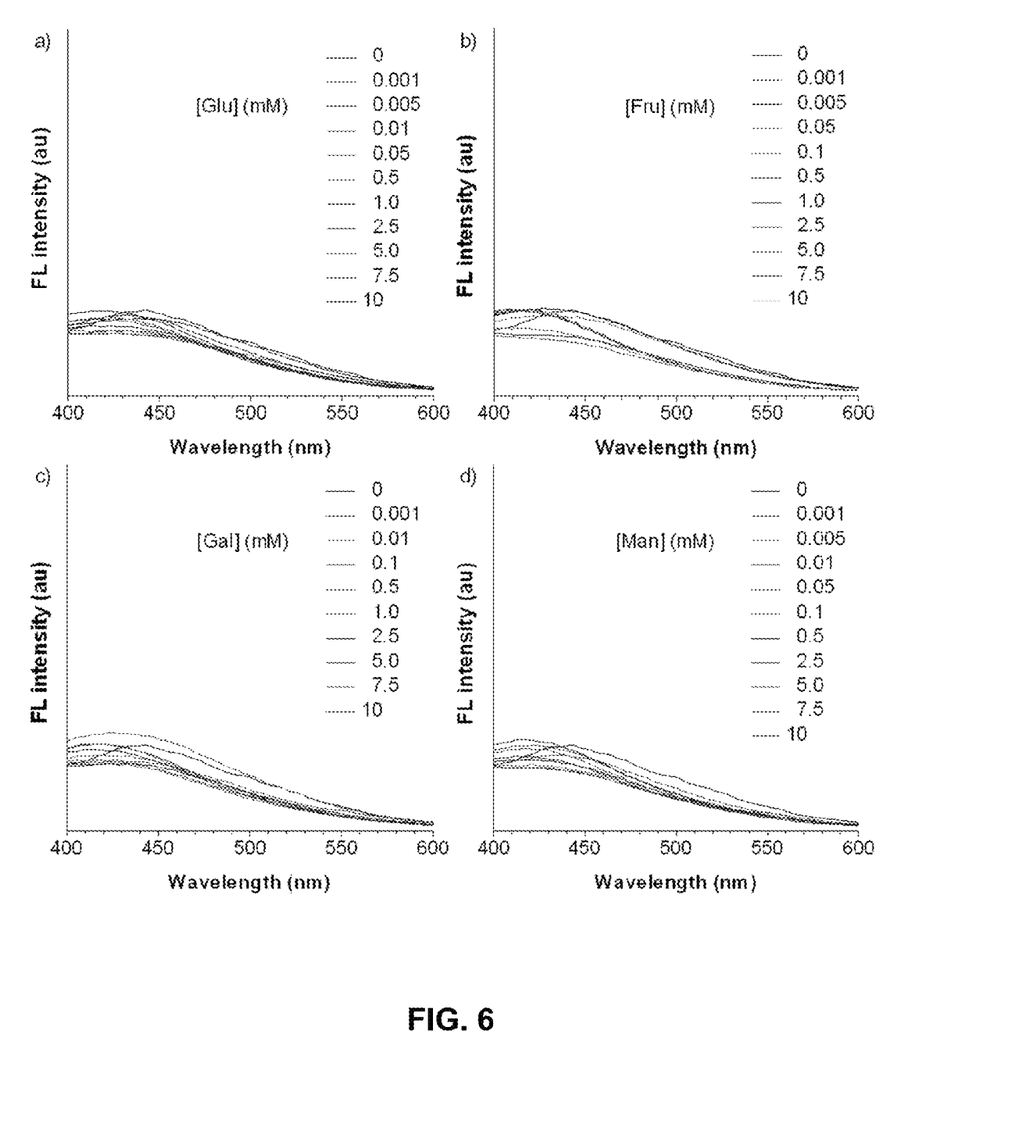
FIG. 6 illustrates FL spectra of mixtures of TPEMB (10 μM) in the carbonate buffer containing 10 vol % DMSO in the presence of (a) D-glucose, (b) D-fructose, (c) D-galactose and (d) D-mannose.
Figure 7:
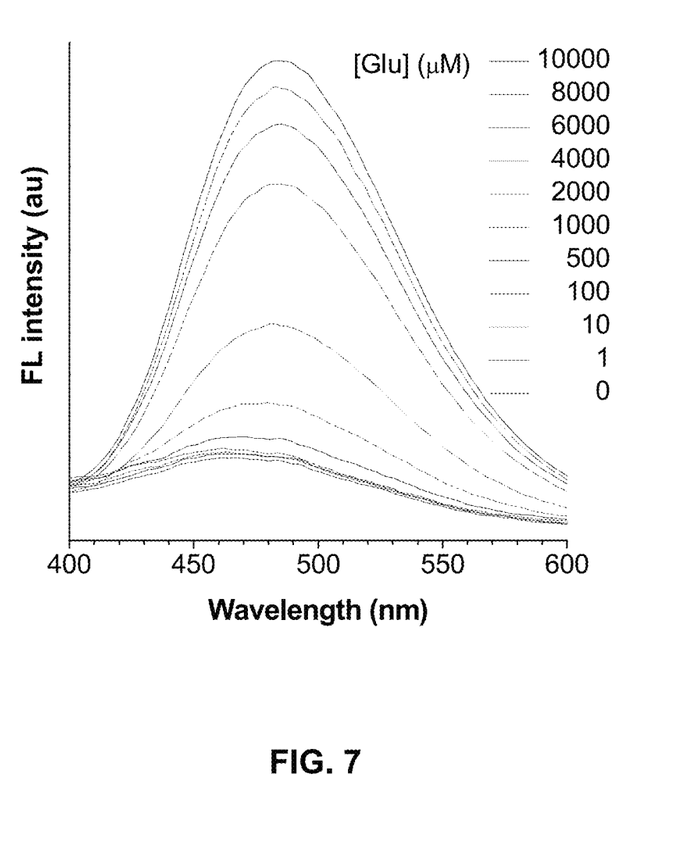
FIG. 7 illustrates FL spectra of TPEDB (50 μM) in the carbonate buffer containing 2 vol % DMSO in the presence of urine D-glucose.

The present subject matter in one embodiment relates to a selective detection of D-glucose (D-Glu) by TPEDB probe in a sample with its fluorescence enhancement. The concentration or level of D-Glu detectable in a sample is not particularly limited, but is preferably about 0.2 mM or more. As shown in FIG. 2, when a tiny amount (<0.2 mM) of an aqueous solution of Glu was added to a solution of TPEDB in a carbonate buffer (pH 10.5), almost no change in the FL spectrum of TPEDB was observed. When 0.2 mM Glu was added, however, the FL spectrum of TPEDB was intensified. The FL intensity increased with an increase in the amount of Glu. At [Glu]=5 mM, the solution of TPEDB became very emissive, with an intensity ca. 5.4-fold higher than that in the absence of Glu. Interestingly, however, further increases in the level of glucose ([Glu]) decreased the FL intensity. In comparison with the big changes caused by Glu, the emission spectrum of TPEDB was only slightly intensified even when a large amount (10 mM) of D-fructose (Fru) was added to the buffer solution of TPEDB, and similar results were observed in the cases of D-galactose (Gal) and D-mannose (Man). See FIG. 5A.

Figure 4:
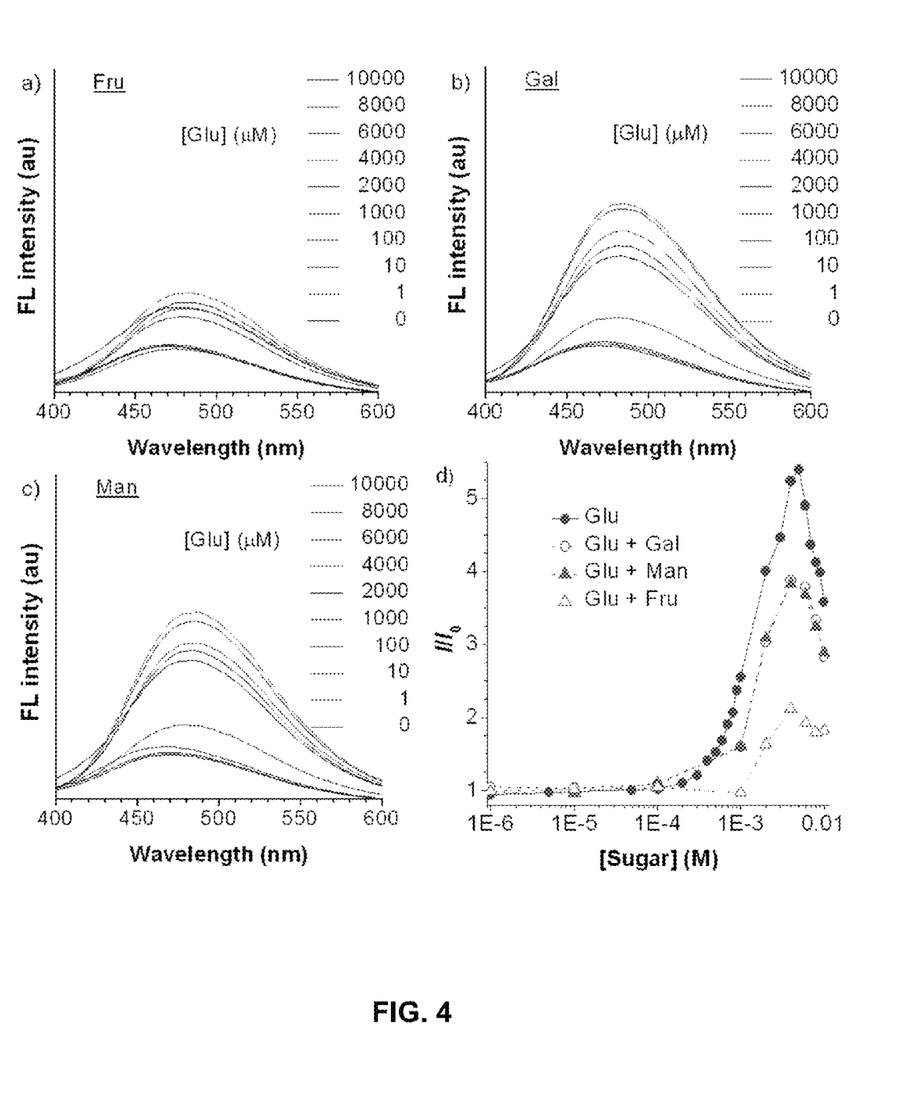
FIG. 4 illustrates FL spectra of mixtures of TPEDB (50 μM) in the carbonate buffer in the presence of different amounts of D-glucose and 0.1 mM of (a) D-galactose, (b) D-mannose, and (c) D-fructose. The figure (d) of FIG. 4 illustrates variation in the FL intensity of TPEDB (50 μM) with D-glucose in the presence of other saccharide interferent (0.1 mM) in the carbonate buffer. Data for D-glucose in the absence of interferent is shown for comparison.

It is found that there is almost no interference of the isomeric saccharides to the FL response of TPEDB to Glu. In the presence of Fru, the FL spectrum of TPEDB was gradually intensified by the addition of Glu, but the rate of increase in the intensity was lower because of the competition between Glu and Fru to bind with TPEDB. Similarly, Gal and Man interfered with the FL response of TPEDB to Glu, although the effects were smaller. See FIG. 5B. These data suggest the following affinity order of saccharide to TPEDB: Fru>Gal≈Man>Glu, which agrees with the trend in $K_a$ reported for saccharide binding with PBA: e.g., $K_{a,sugar}/K_{a,Glu}$=34.8 for Fru, 3.3 for Gal, and 2.8 for Man. Thus, as seen from the data of FIG. 5, TPEDB works well as a Glu-specific FL biosensor in both the absence and the presence of a saccharide interferent and this suggests that the binding affinity is not a decisive parameter in determining the specific FL response of TPEDB to Glu. See FIGS. 4 and 5.

The working mechanism for the specific FL response of TPEDB to Glu is proposed on the basis of the above experimental data and the chemical reactions of arylboronic acids with saccharides, which is shown in Scheme 1.

unit of TPEDB with the cis-1,2-diol units of Glu predominates, giving rise to a 1:1 monoadduct of TPEDB and Glu, i.e., TPEDB-Glu. The aryl rotors of the resultant TPEDB-Glu can still undergo active intramolecular rotations, so it remains nonemissive in the aqueous buffer.

At higher [Glu] (ca. 0.2 mM), two Glu units may end-cap a TPE core, resulting in the formation of the bisadduct TPEDB-Glu$_2$. The intramolecular rotations of the phenyl rings in TPEDB-Glu$_2$ should be less active than in its parent form, thus making it somewhat emissive. At an even higher [Glu], oligomerization may occur, thanks to the accessibility of the cis-5,6-diol units of Glu by the boronate group of the fluorogen. In the oligomer (TPEDB-Glu)$_n$, two phenyl rings in adjacent TPE units are fastened by a Glu linker. The intramolecular rotation of one phenyl ring in the oligomer involves simultaneous movements of the Glu linker and another phenyl ring in the neighboring TPE repeat unit. The high energy barrier to such molecular motions stiffens the oligomer structure, activates the RIR process, and opens the radioactive decay channel.

Under alkaline conditions, TPEDB is transformed to TPEDB—(OH)$_2$, which is nonemissive because of its dissolution in the aqueous medium aided by its charged boronate groups. At low [Glu] (<0.2 mM), the reaction of the boronate

The possibility of oligomer formation increases with increasing [Glu], with the FL intensity reaching its maximum at [Glu]=5 mM. As the boronate-saccharide complexation is a reversible equilibrium process, the end-capping reaction leading to the formation of adduct TPEDB-(Glu)$_2$ becomes prevalent over the oligomerization reaction at very high [Glu]. As discussed above, the intramolecular rotations in TPEDB-(Glu)$_2$ are only partly restricted, which explains the observed intensity decrease for [Glu]>5 mM. See FIG. 5A. As [Glu] is further increased, the TPEDB-(Glu)$_2$ bisadduct is further populated because of the increased prevalence of the end-capping reaction in its competition with the oligomerization process.

Scheme 2 shows a proposed mechanism for reactions of TPEDB with D-Fructose, D-Galactose and D-Mannose.

specific response on TPEDB. In other words, it is the oligomerization of TPEDB with Glu that boosts the emission of the AIE fluorogen.

According to an embodiment of the present subject matter, the tetraphenylethene-cored diboronic acid probe oligomerizes with D-Glu in solution and activates the fluorescence of the probe.

To examine whether the oligomerization reaction indeed plays an essential role in the Glu-selective sensing process, 4-(1,2,2-triphenylvinyl)phenylboronic acid (TPEMB), a monosubstituted TPE derivative with one boronic acid unit that is incapable of undergoing the oligomerization reaction, was prepared. When Glu was added into an aqueous solution of TPEMB, little change in the FL spectrum of TPEMB was observed over a wide [Glu] range. The mono- and bisadducts Scheme 2

Figure 8:
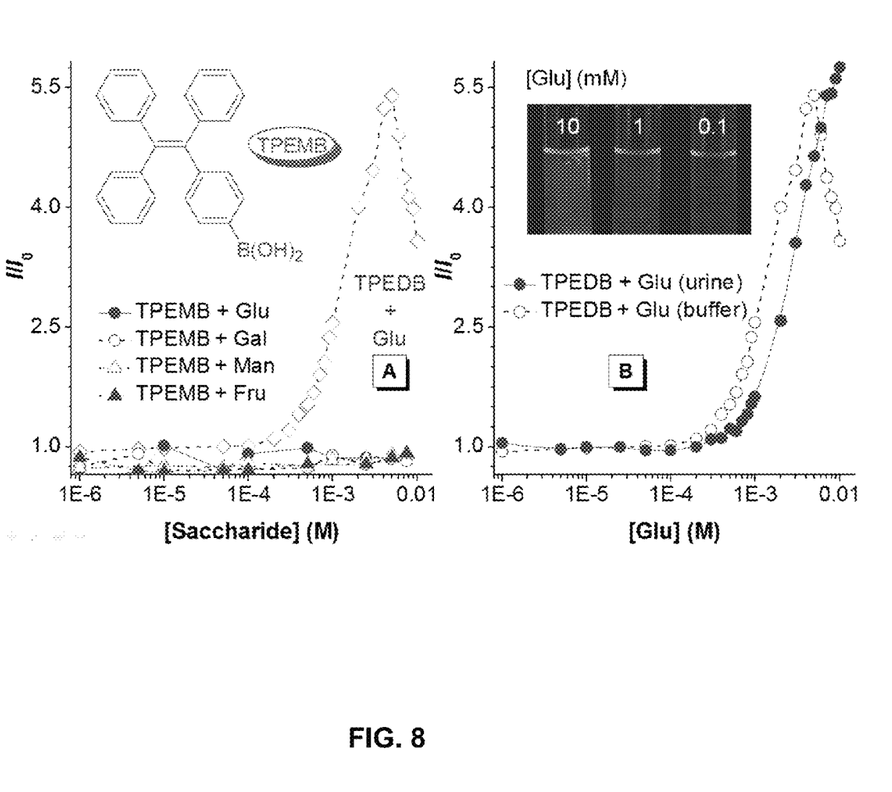
FIG. 8 illustrates variations in the FL intensities (I) of mixtures of (a) TPEMB (10 μM) and (b) TPEDB (50 μM) with a concentration of (A) a saccharide in the carbonate buffer containing 10 vol % DMSO and (B) Glu in artificial urine. $I_0$=intensity in the absence of a saccharide. FL Data for TPEDB in the presence of Glu is shown for comparison. Inset in panel B: photographs of mixtures of TPEDB (50 μM) in the artificial urines containing different amounts of Glu taken under UV illumination.
Figure 9:
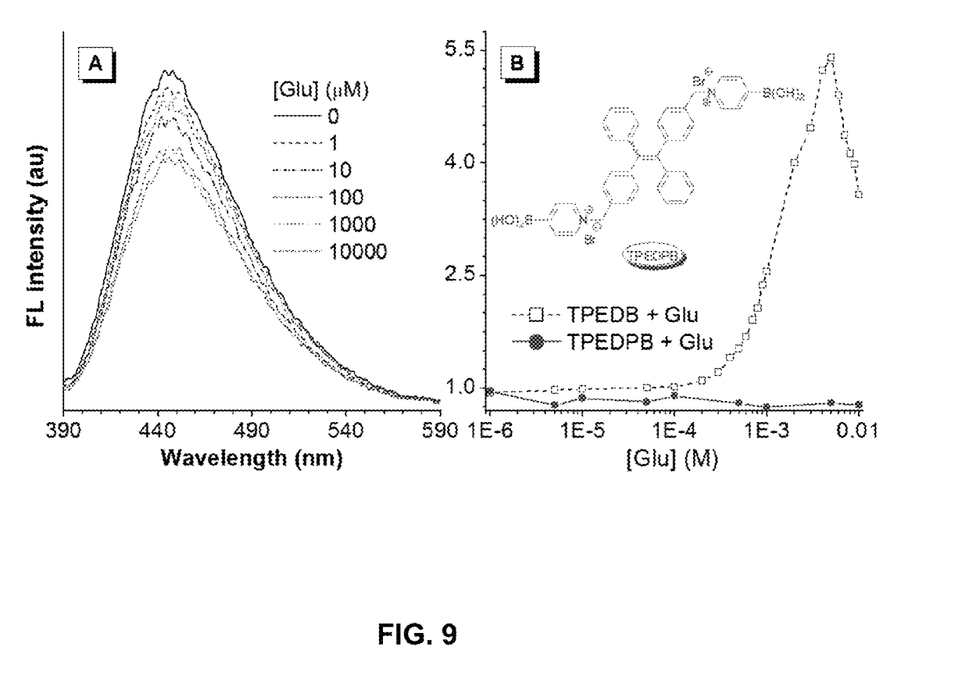
FIG. 9 illustrates (A) FL spectra of mixtures of TPEDPB (0.1 μM) in the PBS buffer (0.1 mM) in the presence of D-glucose and (B) variations in the FL intensities (I) of mixtures of TPEDPB (0.1 μM) with concentrations of Glu in the PBS buffer. $I_0$=intensity in the absence of Glu. FL Data for TPEDB in the presence of Glu is shown for comparison.

Similar to Glu, Fru can react with TPEDB to furnish the monoadduct (TPEDB-Fru) at low [Fru]. At high [Fru], the end-capping bisadduct TPEDB-(Fru)$_2$ is formed, which accounts for the weak FL in the high concentration region. Once reacted with a boronic acid unit, Fru has no additional diol unit with a cis conformation to further react with TPEDB to form oligomeric species. This is why no big change in FL was observed at any concentration of Fru. As in the case of Fru, Gal and Man have no cis-diol moieties that would allow them to undergo the oligomerization reactions. Clearly, the existence of a pair of cis-diol units in the 1,2- and 5,6-positions in Glu is the key structural feature that confers a Glu- TPEMB-Glu and TPEMB$_2$-Glu may be formed, but neither of these can emit efficiently because the intramolecular rotations of the phenyl rotors in these adducts are hardly impeded. Expectedly and understandably, TPEMB remained nonemissive, no matter what amounts of Fru, Gal, and Man were added into its solution. See FIG. 8A. The sharp contrast between the FL data for the systems (TPEMB+Glu) and (TPEDB+Glu) offers strong support to the proposed working mechanism.

To explore the potential of TPEDB for real-world applications, the possibility of using TPEDB for detection of Glu in urine was tested. Addition of Glu in artificial urine into a solution of TPEDB augmented its FL spectrum. The profile of the $I/I_0$ versus [Glu] plot for the urine Glu, however, was different from that for the "pure" Glu (in the carbonate buffer without urine) in the high-[Glu] region. See FIG. 8B. Although the exact reason for this is unclear at the present time, it may be caused by the interactions of urea, α-hydroxy-carboxylic acids, and salts in the urine with the boronate units of TPEDB. Nevertheless, it was found that TPEDB is a promising bio-probe for the specific detection of Glu in urine, which can be applied to monitor the urine glucose level of diabetics and potential diabetics.

EXAMPLES

Example 1

Synthesis of (1,2-diphenylethene-1,2-diyl)bis(1,4-phenylene)-1,1'-diboronic acid (TPEDB)

Synthesis of 1,2-Bis(4-bromophenyl)-1,2-diphenylethene (2)

This TPE derivative was prepared according to previously published experimental procedures. See U.S. Patent Application Publication Nos. 2008/0220407 and 2010/0009362. A white solid was obtained in 77.8% yield.

$^1$H NMR (400 MHz, CDCl$_3$, δ): 7.19-7.25 (m, 3H), 7.06-7.13 (m, 7H), 6.96-7.03 (m, 5H), 6.85-6.90 (d, 3H). $^{13}$C NMR (100 MHz, CDCl$_3$, δ): 142.26, 140.24, 132.94, 132.85, 131.26, 131.18, 131.07, 131.87, 130.81, 127.99, 127.79, 127.62, 126.91, 126.80, 126.61, 126.36.

Synthesis of (1,2-Diphenylethene-1,2-diyl)bis(1,4-phenylene)-1,1'-diboronic acid (TPEDB)

This TPE derivative was prepared according to previously published procedures. See U.S. Patent Application Publication Nos. 2008/0220407 and 2010/0009362. A white solid was obtained in 52% yield.

$^1$H NMR (400 MHz, DMSO-d$_6$, δ): 7.96 [d, B(OH)$_2$], 7.54 (d, 4H), 7.08-7.16 (m, 6H), 6.92-6.99 (m, 8H). $^{13}$C NMR (100 MHz, DMSO-d$_6$, δ): 145.31, 143.57, 141.16, 134.01, 131.08, 130.10, 128.21, 126.99. HRMS (MALDI-TOF, m/z): [M$^+$] calcd for C$_{26}$H$_{22}$B$_2$O$_4$, 420.1704; found, 420.2599.

Because of self condensation of boronic acid under heating, no accurate elemental analysis data for TPEDB could be obtained. Its pinacol-protected derivative (3) was therefore prepared and characterized by elemental analysis, as given below.

Synthesis of 1,2-Diphenyl-1,2-bis[4-(4,4,5,5-tetramethyl-1,3,2-dioxaborolan-2-yl)-phenyl]ethene (3)

Into a 100 mL round bottom flask fitted with a Dean-Stark trap were added TPEDB (240 mg, 0.57 mmol), pinacol (337.6 mg, 2.86 mmol), and 50 mL toluene. The mixture was refluxed overnight. After solvent evaporation, the crude product was purified on a silica-gel column using a mixture of petroleum and ethyl acetate (20:1 v/v) as eluent. A white solid was obtained in 80% yield. Single crystal file no.: CCDC 801326.

$^1$H NMR (400 MHz, CDCl$_3$, δ): 7.55 (d, 4H), 7.50 (d, 2H), 7.06-7.10 (m, 6H), 7.05-6.99 (m, 8H), 1.32 (s, 24H). $^{13}$C NMR (100 MHz, CDCl$_3$, δ): 146.70, 143.34, 141.21, 134.02, 131.29, 130.65, 127.68, 126.51, 83.64, 24.85. HRMS (MALDI-TOF, m/z): ([M+H]$^+$) calcd for C$_{38}$H$_{43}$B$_2$O$_4$, 585.3342; found, 585.3379. Elemental analysis: calcd (%): C, 78.10; H, 7.24. found (%): C, 77.81; H, 7.29.

Example 2

Synthesis of 4-(1,2,2-triphenylvinyl)phenylboronic acid (TPEMB)

Synthesis of 1-(4-Bromophenyl)-1,2,2-triphenylethene (6)

This compound was prepared following previously published procedures. See M. Banerjee, J. Org. Chem, 2007, 72, 8054. 1-(4-Bromophenyl)-1,2,2-triphenylethanol (5) was obtained as an intermediate in the reaction as a white solid, whose dehydration was carried out in toluene in the presence of TsOH. After being washed by hexane, the crude product was purified on a silica-gel column using petroleum ether as an eluent. A white solid was obtained in 82.1% yield.

$^1$H NMR (400 MHz, CDCl$_3$, δ): 7.23 (d, 2H), 7.08-7.16 (m, 9H), 6.99-7.07 (m, 6H), 6.91 (d, 2H). $^{13}$C NMR (100 MHz, CDCl$_3$, δ): 144.38, 143.30, 143.19, 142.67, 141.58, 139.63, 132.94, 131.26, 131.21, 131.20, 130.82, 127.85, 127.75, 127.65, 126.67, 126.61, 126.60, 120.42.

Synthesis of 4-(1,2,2-Triphenylvinyl)phenylboronic Acid (TPEMB)

This compound was prepared by previously published procedures. See W. Z. Yuan, Adv. Mater. 2010, 22, 2159. A white solid was obtained in 83.4% yield.

$^1$H NMR (400 MHz, DMSO-d$_6$, δ): 7.97 [d, B(OH)$_2$], 7.55 (d, 2H), 7.05-7.15 (m, 9H), 6.93-7.00 (m, 8H). $^{13}$C NMR (100 MHz, DMSO-d$_6$, δ): 145.31, 143.58, 141.07, 134.02, 131.05, 130.10, 128.20, 126.98, 126.94. HRMS (MALDI-TOF, m/z): [M$^+$] calcd for C$_{26}$H$_{21}$BO$_2$, 376.1635; found, 376.2280.

Similar to the case of its congener TPEDB discussed above, because of the self-condensation problem of the boronic acid under heating, no accurate elemental analysis data could be obtained for TPEMB. Its pinacol-protected derivative (7) was thus synthesized and characterized by elemental analysis, as given below.

Synthesis of 4,4,5,5-tetramethyl-2-[4-(1,2,2-triphenylvinyl)phenyl]-1,3,2-dioxaborolane (7)

Into a 100 mL round bottom flask fitted with a Dean-Stark trap were added TPEMB (200 mg, 0.53 mmol), pinacol (236.3 mg, 2.0 mmol), and 50 mL toluene. The mixture was refluxed overnight. After addition of a solvent, the crude product was purified on a silica-gel column using a mixture of petroleum and ethyl acetate (20:1 by volume) as eluent. A white solid was obtained in 92% yield.

$^1$H NMR (400 MHz, CDCl$_3$, δ): 7.56 (d, 2H), 7.07-7.13 (m, 9H), 7.00-7.07 (m, 8H), 1.33 (s, 12H). $^{13}$C NMR (100 MHz, CDCl$_3$, δ): 146.73, 143.65, 143.55, 143.48, 141.33, 140.79, 134.04, 131.32, 131.27, 130.66, 127.69, 127.59, 126.47, 126.39, 83.64, 24.85. HRMS (MALDI-TOF, m/z): [M$^+$] calcd for C$_{32}$H$_{31}$B$_2$O$_4$, 458.2417. found, 458.2468. Elemental analysis: calcd (%): C, 83.79; H, 6.58. found (%): C, 83.38; H, 7.00.

Example 3

Synthesis of 1'-(4,4'-(1,2-diphenylethene-1,2-diyl)bis(4,1-phenylene))bis(methylene)bis(4-boronopyridinium) bromide (TPEDPB)

1,2-bis(4-(bromomethyl)phenyl)-1,2-diphenylethene (359 mg, 0.7 mmol), 4-pyridine boronic acid (291 mg, 1.8 mmol, containing 10% water), and 60 mL acetone were added into a 100 mL round bottom flask fitted with a condenser tube. The mixture was refluxed overnight and poured into 120 mL petroleum ether under stirring. The precipitates were filtrated and washed by acetone/petroleum ether (1/2). After drying in a vacuum oven, a white solid (TPEDPB) was obtained in 44.0% yield.

Characterization data of TPEMPB: $^1$H NMR (400 MHz, DMSO), (TMS, ppm): 8.239, 8.223 (d, 4H, Pyridine-H meta to the boronic acid), 7.117 (m, 10H, Ph-H), 6.994-6.943 (m, 8H, Ph-H), 6.733, 6.716 (d, 4H, Pyridine-H ortho to the boronic acid), 5.754 (b, —B(OH)$_2$), 5.271 (s, 4H, —CH$_2$—). $^1$H NMR (400 MHz, DMSO/D$_2$O=10/1) (TMS, ppm): 8.186, 8.169 (d, 4H, Pyridine-H meta to the boronic acid), 7.112-7.085 (m, 10H, Ph-H), 6.969-6.910 (m, 8H, Ph-H), 6.723, 6.707 (d, 4H, Pyridine-H ortho to the boronic acid), 5.211 (s, 4H, —CH$_2$—). $^{13}$C NMR (75 MHz, DMSO/D$_2$O=10/1), (TMS, ppm): 174.5, 144.0, 143.8, 143.0, 140.8, 134.1, 131.5, 130.8, 128.4, 127.8, 127.9, 116.5, 59.9.

Example 4 pH Determination

The detailed experimental procedures for the preparation of the sample solutions and mixtures to be used for pH monitor are given below.

Preparation of Stock Solution of TPEDB in DMSO

A stock solution of TPEDB with a concentration of 10 mM was prepared by dissolving 0.105 g (250 μmol) of TPEDB in 25 mL DMSO. The solution was stored in a refrigerator under 4° C. before use.

Preparation of Stock Solution of TPEDB in Sodium Hydroxide Solution

Into a 100 mL volumetric flask were added 4.0 mg NaOH and 80 mL of deionized water. After adding 3 mL of DMSO into the carbonate buffer, 1 mL of the stock solution of TPEDB in DMSO (10 mM) was added under stirring. The volume of the solution was increased to 100 mL by adding an appropriate amount of deionized water. The resultant solution of TPEDB (0.1 mM) in the NaOH solution (0.001M) containing 4 vol % DMSO was stirred for 15 min before use.

Preparation of Britton-Robinson Buffers (0.08 M)

Into a 100 mL volumetric flask were added 4.611 H$_3$PO$_4$, 2.402 g CH$_3$COOH, and 2.473 g B(OH)$_3$, and the volume of the solution was increased to 100 mL by adding appropriate amount of deionized water. The resultant solution of the acid mixture (0.4 M) was stirred for 15 min before use. Into a 100 mL volumetric flask was added 1.600 g NaOH, and the volume of the solution was increased to 100 mL by adding appropriate amount of deionized water. The resultant solution of base (0.4 M) was stirred for 15 min before use. An aliquot (0.4 mL) of the solution of acid mixture (0.4 M) and appropriate amount of the solution of NaOH (0.4 M) from 0 mL to 1.6 mL were added into a 10 mL volumetric flask. The volume of the solution was increased to 2.0 mL by adding an appropriate amount of deionized water. The resultant standard Britton-Robinson buffer (0.08 M) with various pH was left to stand for a few minutes before use.

Preparation of TPEDB in Buffer with Various pH

An aliquot (2.0 mL) of the stock solution of TPEDB (0.1 mM) in the NaOH solution (0.001M) containing 4 vol % DMSO and 2.0 mL of the standard Britton-Robinson buffer (0.08 M) with various pH were added into a 10 mL volumetric flask. After shaking for a few seconds, solutions of TPEDB (50 μM) with various pH in the Britton-Robinson buffer containing 2 vol % DMSO were obtained. The solutions were allowed to stand for 30 min, and their FL spectra were measured before the pH values were measured using pH-meter.

Example 5

Glucose Detection

The detailed experimental procedures for the preparations of the biological sample solutions and mixtures used for monosaccharide detection are given below.

Preparation of Stock Solution of TPEDB in DMSO

A stock solution of TPEDB with a concentration of 10 mM was prepared by dissolving 0.105 g (250 μmol) of TPEDB in 25 mL DMSO. The solution was stored in a refrigerator under 4° C. before use.

Preparation of Stock Solution of TPEDB in Carbonate Buffer

Into a 100 mL volumetric flask were added 1.120 g of K$_2$CO$_3$, 0.190 g of KHCO$_3$ and 80 mL of deionized water. After adding 3 mL of DMSO into the carbonate buffer, 1 mL of the stock solution of TPEDB in DMSO (10 mM) was added under stirring. The volume of the solution was increased to 100 mL by adding an appropriate amount of deionized water. The resultant solution of TPEDB (0.1 mM) in the carbonate buffer (pH 10.5) was stirred for 15 min before use.

Preparation of Saccharide Solution in Deionized Water

Into a 25 mL volumetric flask was added 90 mg of a saccharide (Glu, Fru, Gal or Man) and 25 mL of deionized water. An aliquot of the resultant stock solution (20 mM) was diluted in another volumetric flask to obtain a sample solution with a desired concentration (2.0 mM, 0.20 mM, 20 μM or 2.0 μM).

Preparation of Mixture of TPEDB and Saccharide

An aliquot (2.0 mL) of the stock solution of TPEDB (0.1 mM) in the carbonate buffer containing 4 vol % DMSO and 2.0 mL of the stock solution of Glu (20 mM) were added into a 10 mL volumetric flask. After shaking for a few seconds, a solution of TPEDB (50 μM) with 10 mM of Glu in the carbonate buffer containing 2 vol % DMSO was obtained. The solution was allowed to stand for 30 min before its FL measurement.

To prepare a solution of TPEDB (50 μM) with 8 mM of Glu in the carbonate buffer containing 2 vol % DMSO, 1.6 mL of the stock solution of Glu (20 mM) and 0.4 mL of deionized water were added to 2.0 mL of a stock solution of TPEDB (0.1 mM) in the carbonate buffer containing 4 vol % DMSO.

Similarly, the concentration of the solution of another saccharide (20 mM, 2.0 mM, 0.20 mM, 20 μM, or 2.0 μM) was adjusted by adding an appropriate amount of deionized water to a volumetric flask with a defined volume.

Preparation of Solution of TPEDB and Glu Containing an Interferent

Solutions of Glu (40 mM-4.0 μM), Fru (0.4 mM), Gal (0.4 mM) and Man (0.4 mM) in deionized water were prepared.

An aliquot (2.0 mL) of the solution of TPEDB (0.1 mM) in the carbonate buffer containing 4 vol % DMSO was added into a 10 mL volumetric flask, followed by the addition of 1.0 mL of a solution of Fru (0.4 mM) and 1.0 mL of a solution of Glu (40 mM). After shaking for a few seconds, a solution of TPEDB (50 µM) with 10 mM of Glu and 0.1 mM of Fru in the carbonate buffer containing 2% DMSO was obtained. The solution was allowed to stand for 30 min before its FL measurement. The solution of TPEDB and Glu containing another saccharide (Gal or Man) was prepared by similar procedures.

Preparation of Glu Solution in Artificial Urine

An artificial urine was prepared according to the recipe reported by Keevil et al. and Whitesides et al (C. W. Keevil, et al, *Lett. Appl. Microbiol.* 1997. 24, 203; G. M. Whitesides, et al, *Proc. Natl. Acad. Sci. U.S.A.* 2008, 105, 19606). 1.1 mM Lactic acid, 2.0 mM citric acid, 25 mM sodium bicarbonate, 170 mM urea, 2.5 mM calcium chloride, 90 mM sodium chloride, 2.0 mM magnesium sulfate, 7.0 mM potassium dihydrogen phosphate, 7.0 mM dipotassium hydrogen phosphate, 10 mM sodium sulfate, and 25 mM ammonium chloride were mixed in deionized water. The pH value of the solution was adjusted to 6.0 by the addition of 1.0 M hydrochloric acid. Finally, Glu was added to form artificial urine solutions with desired concentrations.

An aliquot (1 mL) of the artificial urine solution with a desired concentration of Glu was added to 2 mL solution of TPEDB (100 µM) in the carbonate buffer containing 4 vol % DMSO. A small amount (1 mL) of carbonate buffer was added to the mixture to adjust the concentration of TPEDB to 50 µM. FL spectrum of the mixture was measured after stirring for 30 min.

With the information contained herein, various departures from precise description of the present subject matter will be readily apparent to those skilled in the art to which the present subject matter pertains, without departing from the spirit and the scope of the below claims. The present subject matter is not to be considered limited in scope to the procedures, properties or components defined, since the preferred embodiments and other descriptions are intended only to be illustrative of particular aspects of the presently provided subject matter. Indeed, various modifications of the described modes for carrying out the present subject matter which are obvious to those skilled in molecular biology or related fields are intended to be within the scope of the following claims.

What is claimed is:

1. A method for detecting the presence or absence of glucose or the glucose level in a sample, comprising contacting the sample with a water-soluble tetraphenylethene-cored probe having multiple functionalities of boronic acid and aggregation induced emission (AIE) characteristics, and detecting fluorescence, wherein the water-soluble tetraphenylethene-cored probe is dissolved in a buffer at a pH of at least 9.74, wherein the sample is in aqueous media containing DMSO.

2. The method of claim 1, wherein the water-soluble tetraphenylethene-cored probe contains diboronic acid.

3. The method of claim 2, wherein the water-soluble tetraphenylethene-cored probe is (1,2-diphenylethene-1,2-diyl)bis(1,4-phenylene)-1,1'-diboronic acid (TPEDB).

4. The method of claim 3, wherein the glucose level is from 0.2 mM to 10.0 mM.

5. The method of claim 4, wherein the emission of TPEDB is boosted nearly 5.4 fold when the concentration of D-glucose reaches 5.0 mM.

6. The method of claim 2, wherein the tetraphenylethene-cored probe oligomerizes with D-glucose in solution and activates the fluorescence of the probe.

7. The method of claim 6, wherein the glucose level is 5.0 mM.

8. The method of claim 1, wherein the sample is a solution of D-glucose contained in deionized water.

9. The method of claim 1, wherein the sample is a biological sample.

10. The method of claim 9, wherein the biological sample is a urine solution.

11. The method of claim 1, wherein the sample is contacted with a solution of the water-soluble tetraphenylethene-cored probe in carbonate buffer.

12. The method of claim 11, wherein the carbonate buffer contains 4.0 vol % of dimethyl sulfoxide.

13. The method of claim 11, wherein the carbonate buffer has a concentration of 0.4 M.

14. The method of claim 11, wherein the carbonate buffer has a pH value of 10.5.

15. A method for detecting pH in the range of 8.61 to 9.74 in a sample solution with a certain pH value, comprising contacting the sample solution with a water-soluble tetraphenylethene-cored probe having multiple functionalities of boronic acid and aggregation induced emission (AIE) characteristics, and detecting fluorescence, wherein the water-soluble tetraphenylethene-cored probe is dissolved in a buffer at a pH of at least 8.61, wherein the sample is in aqueous media containing DMSO.

16. The method of claim 15, wherein the water-soluble tetraphenylethene-cored probe is a 2.0 mL stock solution and the sample solution is 2.0 mL standard buffer solution.

17. The method of claim 15, wherein the water-soluble tetraphenylethene-cored probe is (1,2-Diphenylethene-1,2-diyl)bis(1,4-phenylene)-1,1'-diboronic acid (TPEDB).

18. The method of claim 15, wherein the sample solution is a sodium hydroxide solution.

19. The method of claim 18, wherein the sodium hydroxide solution contains 4.0 vol % DMSO.

20. The method of claim 18, wherein the concentration of the sodium hydroxide solution is 0.01 M.

21. The method of claim 15, wherein the sample solution is prepared using Britton-Robinson buffers.

* * * * *